United States Patent
Griffith

(10) Patent No.: US 11,819,116 B2
(45) Date of Patent: Nov. 21, 2023

(54) MAGNETICALLY LEVITATING STERILIZING TOOTHBRUSH HOLDER

(71) Applicant: Robert Griffith, Kent, WA (US)

(72) Inventor: Robert Griffith, Kent, WA (US)

( * ) Notice: Subject to any disclaimer, the term of this patent is extended or adjusted under 35 U.S.C. 154(b) by 331 days.

(21) Appl. No.: 17/375,133

(22) Filed: Jul. 14, 2021

(65) Prior Publication Data

US 2022/0015533 A1     Jan. 20, 2022

Related U.S. Application Data

(60) Provisional application No. 63/053,533, filed on Jul. 17, 2020.

(51) Int. Cl.

| | | |
|---|---|---|
| *A46B 17/06* | (2006.01) | |
| *A47K 1/09* | (2006.01) | |
| *H02N 15/00* | (2006.01) | |
| *H01F 7/06* | (2006.01) | |
| *H01F 7/20* | (2006.01) | |
| *A61L 2/10* | (2006.01) | |

(52) U.S. Cl.
CPC .............. *A46B 17/065* (2013.01); *A47K 1/09* (2013.01); *A61L 2/10* (2013.01); *H01F 7/064* (2013.01); *H01F 7/206* (2013.01); *H02N 15/00* (2013.01); *A46B 2200/1066* (2013.01); *A61L 2202/11* (2013.01); *H01F 2007/208* (2013.01)

(58) Field of Classification Search
CPC ............. A45D 44/18; A45D 2200/205; A46B 17/065; A46B 2200/1066; A47K 1/09; A61L 2/10; A61L 2202/11; H01F 7/064; H01F 7/206; H01F 2007/208; H02N 15/00

USPC ..... 206/15.2, 209, 362.1, 362.2, 362.3, 818; 132/308; 211/65

See application file for complete search history.

(56) References Cited

U.S. PATENT DOCUMENTS

| | | |
|---|---|---|
| 4,214,657 A | 7/1980 | Winston |
| 4,325,485 A | 4/1982 | Pina et al. |
| 4,523,599 A * | 6/1985 | Collet ................... A46B 17/08 132/313 |
| 4,906,851 A | 3/1990 | Beasley et al. |
| | (Continued) | |

FOREIGN PATENT DOCUMENTS

| | | | |
|---|---|---|---|
| CN | 201505062 U | * 6/2010 | |
| CN | 107334402 A | * 11/2017 | ............... A47K 1/09 |
| | (Continued) | | |

*Primary Examiner* — Joshua E Rodden
(74) *Attorney, Agent, or Firm* — Anthony Claiborne

(57) ABSTRACT

A magnetically levitating sterilizing toothbrush holder with associated toothbrush includes a holder generating a magnetic field and a toothbrush including a magnetic or ferromagnetic element. The holder and toothbrush are so configured that, when the toothbrush is placed in the holder, the force of gravity acting on the toothbrush is balanced in opposition to the magnetic force resulting from the interaction of the toothbrush's magnetic element with the holder's magnetic field, resulting in magnetic levitation of the toothbrush within the holder, thereby suspending the brush from all potentially contaminating surfaces. The holder further includes a sterilizing ultraviolet light source, whereby the operational end of the toothbrush with its bristles is bathed in sterilizing radiation when the brush is suspended in the holder.

9 Claims, 4 Drawing Sheets

(56) References Cited

U.S. PATENT DOCUMENTS

| | | | | |
|---|---|---|---|---|
| 5,163,566 | A * | 11/1992 | Hempel | A47K 1/09 |
| | | | | 211/DIG. 1 |
| 8,727,141 | B2 * | 5/2014 | Akalin | A46B 17/02 |
| | | | | 211/DIG. 1 |
| 10,631,627 | B2 * | 4/2020 | Peters | A46B 15/0095 |
| 11,039,681 | B1 * | 6/2021 | Altschuler | B08B 1/001 |
| 11,399,622 | B2 * | 8/2022 | Jungnickel | A46B 5/021 |
| 2009/0010826 | A1 * | 1/2009 | Shin | A61L 2/10 |
| | | | | 422/300 |
| 2009/0184015 | A1 * | 7/2009 | Ruppert | A46B 17/02 |
| | | | | 206/362.2 |
| 2009/0189084 | A1 * | 7/2009 | Pinsky | A46B 17/06 |
| | | | | 206/362.2 |
| 2011/0100865 | A1 * | 5/2011 | Brink | A61C 19/02 |
| | | | | 206/581 |
| 2012/0112018 | A1 * | 5/2012 | Barry | H01F 7/0252 |
| | | | | 248/206.5 |
| 2015/0052727 | A1 * | 2/2015 | Rosso, Jr. | A47B 67/02 |
| | | | | 29/428 |
| 2018/0295979 | A1 * | 10/2018 | Miller | A46B 15/0038 |
| 2019/0070326 | A1 * | 3/2019 | Xie | A61L 2/26 |
| 2021/0345767 | A1 * | 11/2021 | Zheng | A61L 2/10 |

FOREIGN PATENT DOCUMENTS

| | | | | |
|---|---|---|---|---|
| KR | 2019137549 A | * | 12/2019 | A47K 1/09 |
| KR | 2022002435 U | * | 10/2022 | A46B 17/02 |

* cited by examiner

MAGNETICALLY LEVITATING STERILIZING TOOTHBRUSH HOLDER

CROSS-REFERENCE TO RELATED APPLICATION

This application claims the benefit of U.S. provisional patent application No. 63/053,533, filed Jul. 17, 2020.

BACKGROUND OF THE INVENTION

Field of the Invention

This invention relates generally to a toothbrush and holder and specifically to such a combination whereby the toothbrush is levitated magnetically and sterilized by the holder.

Description of the Related Art

For hygienic purposes, some holders for toothbrushes have been designed to hold a toothbrush in an elevated position, so that the bristles and other operational parts of the toothbrush are suspended and not in contact with potentially contaminated surfaces. Exemplary of many such holders in the related art, U.S. Pat. No. 4,325,485 to Pina et al. and U.S. Pat. No. 8,727,141 to Akalin et al., illustrate a holder comprising a wall-mounted rack, whereby the handle portion of the toothbrush is retained by the holder and the brush portion of the toothbrush hangs down from the holder, elevating the working end of the brush with its bristles above a surface such as a bathroom counter.

Further for hygiene, some holders for toothbrushes have been designed to sterilize the brush and its bristles between uses. For example, U.S. Pat. No. 4,214,657 to Winston discloses a toothbrush holder having a cavity with a sponge containing a volatile sterilizing fluid such as diluted phenol. Between uses, the brush is placed in the holder with its bristle end inserted into the cavity. Vapors from the sterilizing fluid carried in the sponge act to sterilize the toothbrush.

Another approach to sterilizing toothbrushes has been to subject them to ultraviolet radiation. For example, U.S. Pat. No. 4,906,851 to Beasley et al. provides a holder with a an ultraviolet lamp that supplies an application of germicidal radiation to bristles of brushes that are retained in the holder.

However, as illustrated by the foregoing examples, related art generally does not combine the hygienic utilities of suspending the brush above all potentially contaminating surfaces with that of sterilizing the bristles between uses.

What is needed is a toothbrush holder that fully suspends a brush within the confines of the holder so that the brush is truly free of potentially contaminating contact. Further what is needed is such a holder that sterilizes the bristles of the brush while it is suspended in the holder.

SUMMARY OF THE INVENTION

A magnetically levitating sterilizing toothbrush holder with associated toothbrush comprises a holder generating a magnetic field and a toothbrush comprising a magnetic or ferromagnetic element. The holder and toothbrush are so configured that, when the toothbrush is placed in the holder, the force of gravity acting on the toothbrush is balanced in opposition to the magnetic force resulting from the interaction of the toothbrush's magnetic element with the holder's magnetic field, resulting in magnetic levitation of the toothbrush within the holder, thereby suspending the brush from all potentially contaminating surfaces. The holder further comprises a sterilizing ultraviolet light source, whereby the operational end of the toothbrush with its bristles is bathed in sterilizing radiation when the brush is suspended in the holder.

BRIEF DESCRIPTION OF THE DRAWINGS

Objects of the present invention as well as advantages, features and characteristics, in addition to methods of operation, function of related elements of structure, and the combination of parts and economies of manufacture, will become apparent upon consideration of the following description and claims with reference to the accompanying drawings, all of which form a part of this specification, wherein like reference numerals designate corresponding parts in the various figures, and wherein:

FIG. 2b is a depiction of another embodiment of a toothbrush for use in an embodiment of the invention along the lines of that shown in FIG. 2a; and FIG. 3 is a circuit diagram of the electronic controls for an electromagnet according to the invention depicted in FIG. 2a.

DETAILED DESCRIPTION OF THE INVENTION

Figure 1:
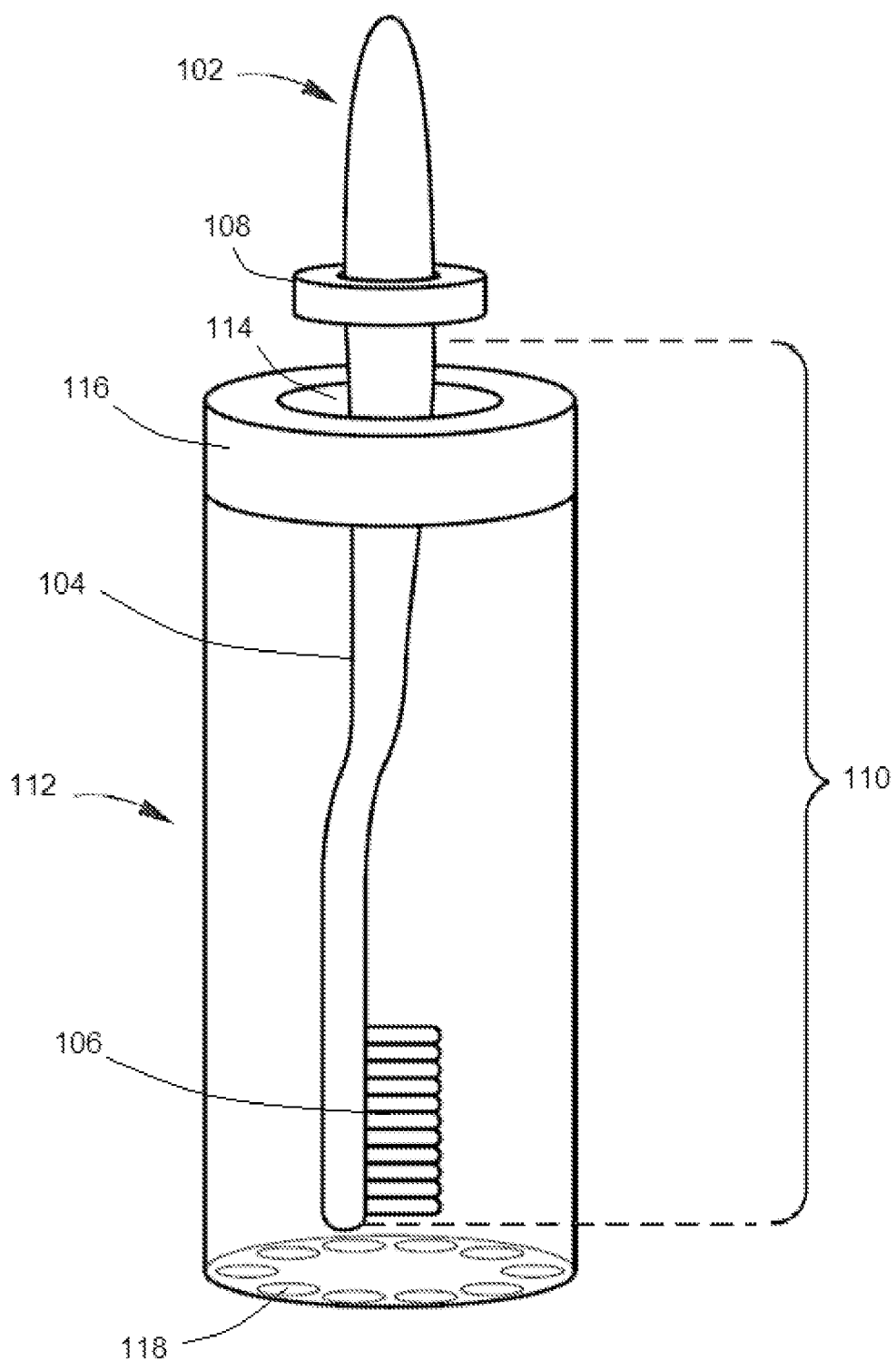
FIG. 1 is a depiction of one embodiment of the invention.

Turning now to the drawings, FIG. 1 illustrates one embodiment of the invention. Toothbrush 102 with handle 104 and cleaning head 106 has attached permanent annular toothbrush magnet 108. In use for brushing teeth, the user grasps toothbrush handle 104 in the span between magnet 108 and cleaning head 106. In embodiments such as depicted, this span should be roughly a hand-width in length. Embodiments may meet this requirement with an span of 110 of 5 to 7 inches.

In some embodiments, toothbrush magnet 108 may comprise rare earth alloy material, such as neodymium iron boron or samarium cobalt. Alternatively, in other embodiments, toothbrush magnet 108 may comprise the aluminum-nickel-cobalt alloy commonly called alnico. In yet other embodiments, annular toothbrush magnet 108 may be composed of ceramic or ferrite material. In yet other embodiments, annular toothbrush magnet 108 may be an electromagnet powered by battery internal to the toothbrush.

Holder 112 is fashioned as an upright cylinder with height equal to or exceeding the operational distance 110 between the lower portion of magnet 108 and the end of cleaning head 106 of toothbrush 102. In the toothbrush and holder combination in use, holder 112 receives toothbrush 102 through an orifice 114 in an annular holder magnet 116. In some embodiments, holder magnet 116 may be a permanent magnet of materials such as those described in relation to toothbrush magnet 108. Alternatively in other embodiments holder magnet 116 may be an electromagnet that is powered on when the invention is in use.

In any case, in embodiments along the lines of that depicted in FIG. 1, what is needed is that, when toothbrush 102 is inserted into orifice 114 of holder magnet 116, the polarity of the downward side of toothbrush magnet 108 be the same as that of the upward side of holder magnet 116. In the depicted embodiment, the downward side of toothbrush magnet 108 is its positive pole and the upward side of holder magnet 116 is its positive pole. These poles repel each other, thereby levitating toothbrush 102 which is slideably disposed within orifice 114 of holder magnet 116 with the end of cleaning head 106 suspended above the bottom of holder 112.

Disposed within the bottom of holder 112 is UV light source 118. In some embodiments, as in the depiction in FIG. 1, UV light source 118 may be an array of ultra-violet light emitting diodes. Other embodiments may employ a low pressure UV-C lamp such as those manufactured by Signify N.V., headquartered in Eindhoven, The Netherlands, as UV light source 118. What is needed is that UV light source 118 supply sufficient radiation in the UV-C wavelength range (100-280 nm) to ensure satisfactory disinfection of a toothbrush 102 stored in holder 112 for a usual duration (typically overnight).

Figure 2A:
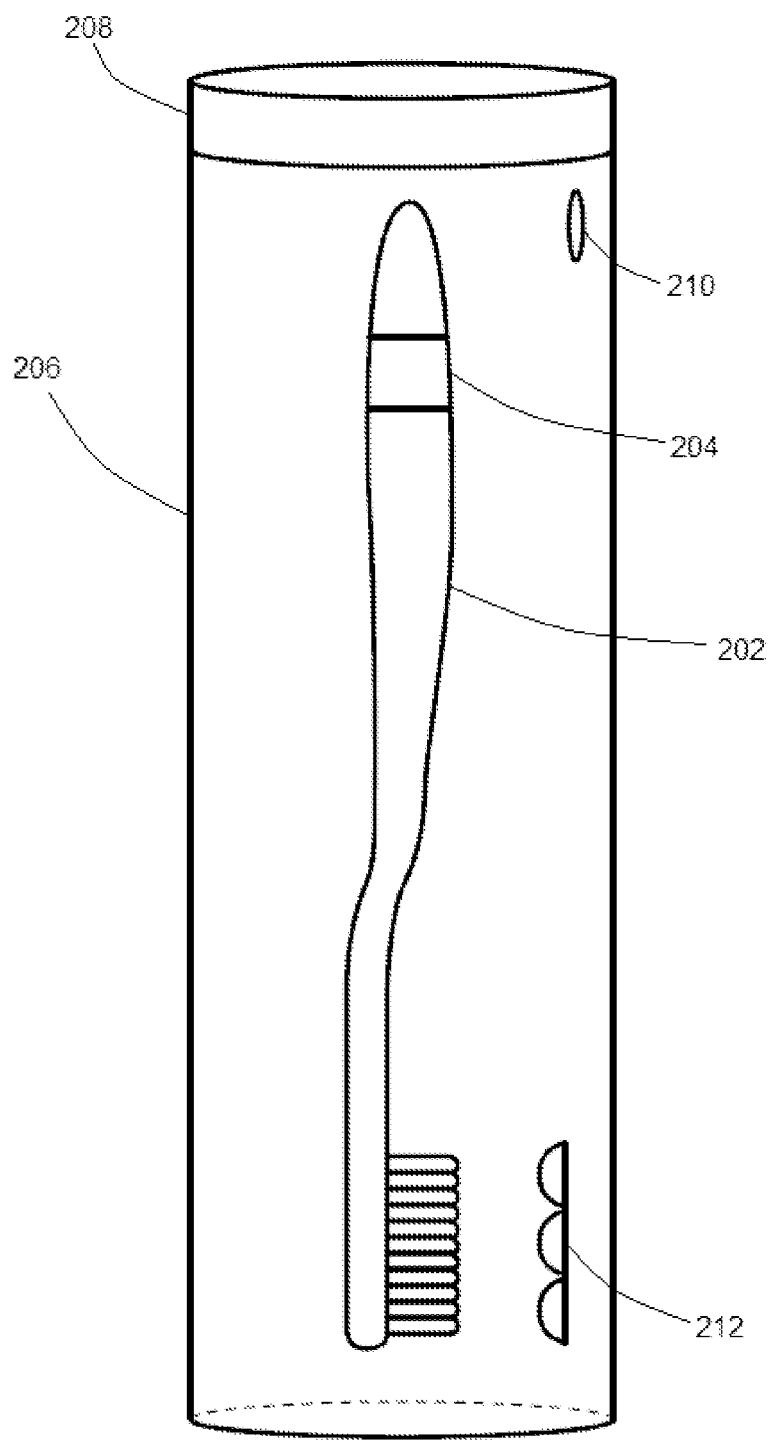
FIG. 2a is a depiction of a second embodiment of the invention employing an electronically controlled electromagnet in the holder.
Figure 2B:
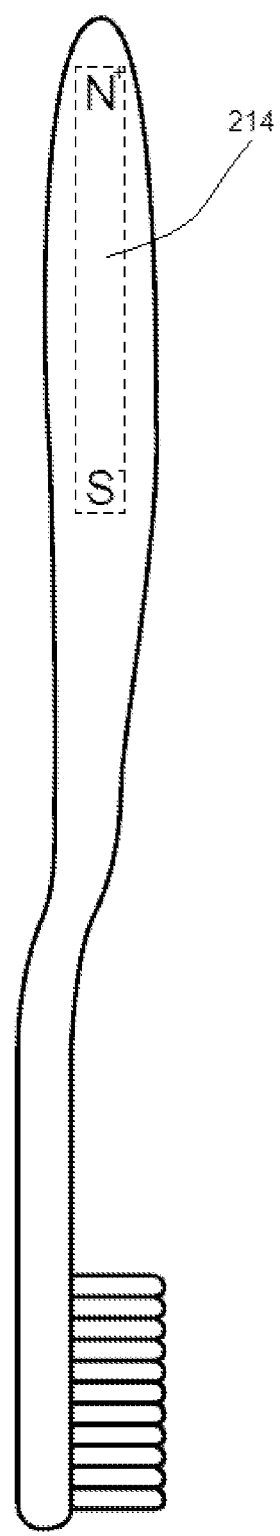

FIG. 2a illustrates another embodiment of the invention. In this embodiment, toothbrush 202 is magnetically levitated within half cylinder holder 206. Toothbrush 202 comprises magnetic ring 204, which may be comprised of ferromagnetic material such as iron, as illustrated in FIG. 2a or it may be a ring of permanent magnetic material such as described in reference to FIG. 1 above, or alternatively toothbrush may have disposed in the handle thereof a bar magnet 214 as illustrated in FIG. 2b.

Disposed at the top of holder 206 is electromagnet 208, controlled by electronic circuitry, further described in reference to FIG. 3 below, responsive to Hall-effect sensor 210. Sensor 210 is affixed to holder 206 in a location intermediate between magnetic ring 204 of toothbrush 202 or the upper pole of bar magnet 214 in the toothbrush, as the case may be, and electromagnet 208. If toothbrush 202 possesses a magnetic ring 204 that is magnetized, or if a bar magnet 214 is in toothbrush 202, the circuitry powering electromagnet 208 generates a magnetic field in which the pole facing downward from electromagnet 208 is the opposite polarity from that of the upward side of magnetic ring 204 or bar magnet 214. If, on the other hand, magnetic ring 204 is of non-magnetized ferromagnetic material, the polarity of electromagnet 208 is not relevant.

In any case, control circuitry responsive to sensor 210 generates fluctuating power to electromagnet 208 magnetically to attract toothbrush 202 by magnetic ring 204 or bar magnet 214 upward against gravity but not with such force as to cause toothbrush 202 to contact electromagnet 208.

In a manner similar to that employed in the embodiment depicted in FIG. 1, in this embodiment a UV light source 212, such as that described earlier, supplies UV-C radiation to the brush of toothbrush 202 satisfactorily to disinfect the toothbrush 202 when toothbrush 202 is stored in holder 206 for the usual duration.

Figure 3:
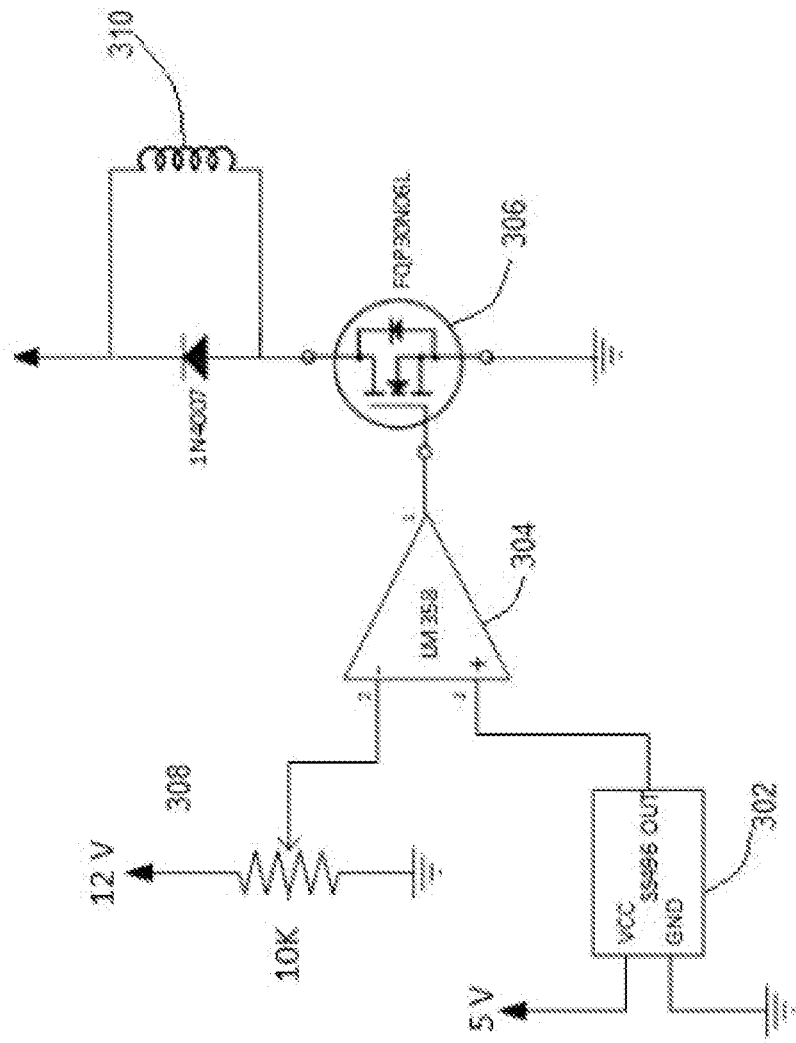

Turning now to FIG. 3, depicted is a circuit diagram for controlling an electromagnet for levitating the toothbrush in embodiments of the present invention, such as that depicted in FIG. 2. A Hall-effect transistor 302 varies voltage depending upon the strength of the local magnetic field, providing lower voltages as the magnetic field strength increases. In this circuit, a comparator operational amplifier 304 will output voltage on its pin 1 when the voltage from Hall effect transistor 302 drops to a certain level, set by variable resistor 308 (potentiometer) attached to comparator operational amplifier 304 at pin 2.

For operation in embodiments along the lines of that depicted in FIG. 2, when triggered the comparator operational amplifier 304 supplies voltage to MOSFET transistor 306 which switches on and thereby supplies voltage to electromagnet 310. When the magnetic field strength rises above the set level, voltage out from Hall effect transistor 302 will rise to a level that causes operational amplifier 304 to cut voltage to MOSFET transistor 306, thereby removing power and magnetic effect from electromagnet 310. This circuitry provides magnetic force when the strength of the local magnetic field has decreased and cuts magnetic force when the strength of the local magnetic field becomes high. Thereby, the upward magnetic forces and the downward gravitational forces are maintained in balance and the toothbrush remains levitated and in position for sterilizing ultraviolet radiation.

As will be appreciated by those of skill in the art, a wide variety of embodiments are possible within the scope of the invention. The physical configuration of the holder, such as its shape and physical proportions, is not intended to be limited to the specific descriptions provided with respect to the embodiments illustrated herein. Similarly, the magnetic or ferromagnetic component of the toothbrush is not to be limited only to the examples provided here Yet further, while magnetic levitation with the bristles in a downward position is illustrated, the toothbrush may be levitated magnetically in other positions in other embodiments hereof. Further still, many variations employing either attractive or repulsive magnetic forces may be used to achieve the magnetic levitation required by the invention.

While the invention has been described with a certain degree of particularity, it should be recognized that elements thereof may be altered by persons skilled in the art without departing from the spirit and scope of the invention. Accordingly, the present invention is not intended to be limited to the specific forms set forth in this specification, but on the contrary, it is intended to cover such alternatives, modifications and equivalents as can be reasonably included within the scope of the invention.

I claim:

1. A toothbrush in combination with a toothbrush holder, the toothbrush comprising:
   a handle with a cleaning head mounted to the handle;
   a toothbrush magnet encircling the handle and affixed thereto at a toothbrush operational distance from the cleaning head, the toothbrush magnet in operation comprising:
      a lower toothbrush polarity;
      an upper toothbrush polarity;
      wherein the lower toothbrush polarity is oriented proximal the cleaning head and the upper toothbrush polarity is oriented distal the cleaning head;
   the toothbrush holder formed as an upright hollow cylinder comprising:
      a bottom;
      a top, comprising:
         an orifice for receiving the toothbrush;
         an annular holder magnet surrounding the orifice, the annular holder magnet in operation comprising:
            an upper holder polarity oriented distal the bottom and matching the lower toothbrush polarity;
            a lower holder polarity oriented proximal the bottom;
      a height greater than the toothbrush operational distance; and
      a source of cleansing ultraviolet radiation located within the toothbrush holder proximate the toothbrush operational distance from the top.

2. The toothbrush in combination with a toothbrush holder according to claim 1, wherein at least one of the toothbrush magnet and the annular holder magnet is a permanent magnet.

3. The toothbrush in combination with a toothbrush holder according to claim 2, wherein the permanent magnet is selected from a group consisting of ceramic magnets, neodymium magnets, samarium cobalt magnets and aluminum-nickel-cobalt alloy magnets.

4. The toothbrush in combination with a toothbrush holder according to claim 1, wherein at least one of the toothbrush magnet and the annular holder magnet is an electromagnet.

5. A toothbrush in combination with a toothbrush holder, the toothbrush comprising:
   a handle with a cleaning head mounted to the handle;
   a magnetic component, integral to the handle distal the cleaning head;
   the toothbrush holder formed as a hollow upright container comprising:
      a side opening for receiving a vertically oriented toothbrush;
      an interior having an upper portion and a lower portion:
      an electromagnet affixed in the upper portion;
      a Hall-effect sensor proximate the electromagnet, the Hall-effect sensor in operation providing data to a control circuit, the control circuit in operation providing current to the electromagnet in proportion to data provided by the Hall-effect sensor; and
      a source of cleansing ultraviolet radiation affixed in the lower portion.

6. The toothbrush in combination with a toothbrush holder according to claim 5, in which the magnetic component is comprised of ferromagnetic material.

7. The toothbrush in combination with a toothbrush holder according to claim 5, in which the magnetic component is a magnet configured to be attracted to the electromagnet in operation.

8. The toothbrush in combination with a toothbrush holder according to claim 7, in which the magnet is a bar magnet integral to the handle.

9. The toothbrush in combination with a toothbrush holder according to claim 7, in which the magnet is electromagnetic.

* * * * *